United States Patent [19]
Nagler

[11] Patent Number: 6,093,143
[45] Date of Patent: Jul. 25, 2000

[54] MAGNETIC THERAPY

[75] Inventor: Yovanka Nagler, Pretoria, South Africa

[73] Assignee: Magno Therapy, Inc., New Castle, Del.

[21] Appl. No.: 09/128,838

[22] Filed: Aug. 4, 1998

[51] Int. Cl.[7] ................................................. A61N 1/00
[52] U.S. Cl. ............................................................. 600/15
[58] Field of Search ........................................... 600/9–15

[56] References Cited

U.S. PATENT DOCUMENTS

| | | | |
|---|---|---|---|
| 5,720,046 | 2/1998 | Lopez et al. | ................ 600/15 |
| 5,782,743 | 7/1998 | Russell | ........................ 600/15 |

FOREIGN PATENT DOCUMENTS

| | | | |
|---|---|---|---|
| 001734777 | 5/1992 | U.S.S.R. | .................. 600/15 |
| 2224940 | 5/1990 | United Kingdom | ...... 600/15 |
| 93/06887 | 4/1993 | WIPO | ...................... 600/15 |

Primary Examiner—John P. Lacyk
Attorney, Agent, or Firm—Huntley & Associates

[57] ABSTRACT

A magnetic therapy method and apparatus useful for the treatment and prevention of painful joint or muscle conditions, preferably using magnets at two or more body locations and preferably using a combination of at least one band magnet and a discrete magnet attached thereto.

21 Claims, 3 Drawing Sheets

MAGNETIC THERAPY

BACKGROUND OF THE INVENTION

This invention relates to a method of treating or preventing painful joint or muscle conditions by use of magnetic therapy, and to an apparatus for the treatment of such painful joint or muscle conditions.

Painful muscles and joints are common problems suffered at some time by a vast majority of people. The pain can be caused either by diseases such as arthritis, or by subjecting the body to stress and strain by various physical activities.

One such painful condition resulting from abnormal strain being put on the body is that of "arm pump-up" commonly suffered by moto-cross or enduro riders. It originates from vibrations caused by rough terrain, which are transmitted via the handlebars of a motorcycle to the arms of the rider.

The symptoms of arm pump-up are swollen forearms which become exceptionally hard to the touch and painful, sometimes even causing loss of control of wrists and hands. The area of the arm most affected is the carpal tunnel which is a fibrous bridge spanning the small bones at the base of the palm of the hand. Friction in the carpal tunnel creates pressure on the median nerve causing numbness, pins and needles, pain and weakness and even loss of control of the whole arm and hand.

Although arm pump-up is treatable, a prophylactic would obviously be more desirable in order to prevent its occurrence. As a result of the failure of conventional medicine to effectively treat certain medical conditions such as those described above, there is a growing tendency to explore the paths of alternative medicine.

One of these alternative practices is the use of magnetic therapy. Although it is not entirely clear how magnetic therapy works, it has been found to increase blood flow and therefore oxygen carrying capacity, to change the migration of calcium ions to or from the bone, to alter the pH balance of various body fluids, to alter hormone production from endocrine glands and to alter the enzymatic activity and other biochemical processes of the human body.

SUMMARY OF THE INVENTION

This invention provides a method of and an apparatus for treating painful joint and muscle conditions.

Specifically, the invention provides an apparatus comprising a magnetic band having attached thereto at least one discrete rare earth magnet.

The invention also provides an apparatus for treating painful joint or muscle conditions, comprising at least two magnetic bands locatable on an affected limb in an axially spaced-apart configuration, each magnetic band being adapted to circumscribe the affected limb.

This invention further provides a method of treating painful joint or muscle conditions, comprising circumscribing an affected body part by at least two magnetic bands in an axially spaced-apart configuration.

DETAILED DESCRIPTION OF THE INVENTION

Figure 1:
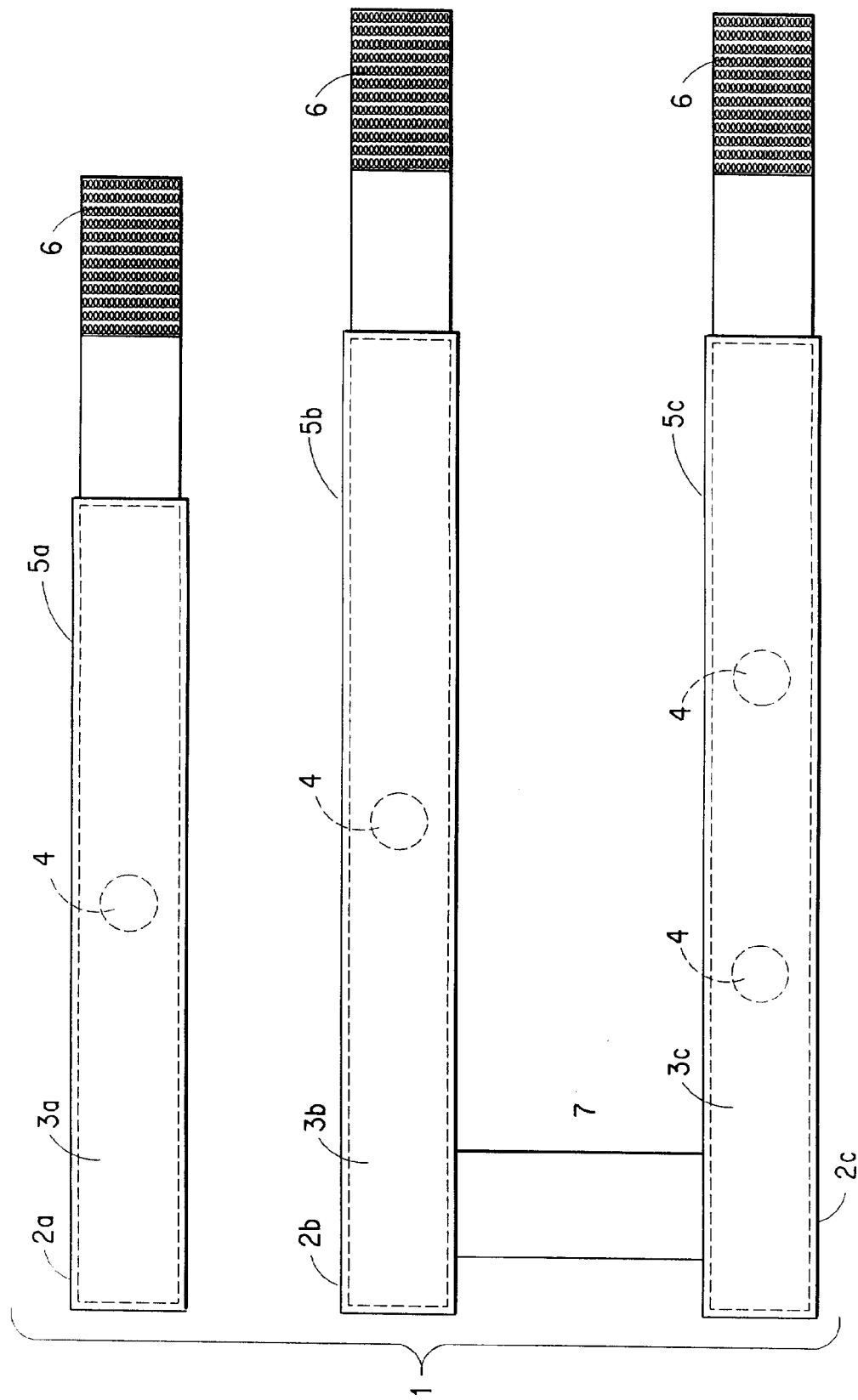
FIG. 1 is a perspective view of one embodiment of an apparatus according to the invention.

The present invention is applicable to a wide variety of painful joint or muscle conditions such as arthritis, muscular cramps, swollen joints and arm pump-up.

The method of the present invention provides for treating joint or muscle pain by circumscribing an affected body part by at least two magnetic bands in an axially spaced-apart configuration. This method is particularly applicable to limbs and is especially useful in the treatment of arm conditions such as arm pumpup by circumscribing an affected arm with three magnetic bands. The first magnetic band is located around the wrist of the wearer, and the second and third bands are located, respectively, around the arm of the wearer on the proximal and distal sides of the elbow joint.

The method of the present invention preferably includes positioning discrete magnets at specific points of the affected body part. For example, in the treatment of arm pump-up, one discrete magnet may be positioned such that it is over the carpal tunnel region of the wearer, second and third discrete magnets can be positioned over the inner forearm of the wearer below the elbow joint, and a fourth discrete magnet may be positioned over the lower bicep of the wearer immediately above the elbow joint.

The set of magnetic bands preferably includes three magnetic bands. Each magnetic band is preferably prepared from a flexible rectangular member having major and minor axes. The major axis of the flexible rectangular member should be long enough to circumscribe the affected body part. The rectangular member is preferably made of polymer-bonded strontium and barium foil, and it is especially preferred that the foil be impregnated with a ferrite isotropic magnet. In general, the isotropic magnet has a magnetic strength of about from 12000 and 16000 gauss, preferably about 14000 gauss, an energy product of about from 0.3 and 0.4 mega-oersteds, preferably about 0.36 mega-oersteds, and a coercive force of about from 11000 to 12000, preferably about 11500 gauss.

Still further preferred features of the invention include at least one rare earth magnet attached to each flexible rectangular member. Rare earth magnets which can be used include nickel-plated neodymium iron boron magnets. These rare earth magnets should have a magnetic strength of about from 11000 and 12500 gauss, preferably about from 11600 to 12300 gauss. The rare earth magnets preferably have a coercive force of about from 10500 to 11000, preferably about from 10800 to 11300 gauss. The rare earth magnets preferably have an energy product of about from 30 and 40 mega-oersteds, preferably about from 32 and 35 mega-oersteds. The rare earth magnets are preferably adhesively bonded to the flexible rectangular member, but other attachment means which will be evident to the skilled designer may be used.

Yet further preferred features of the invention include enclosing each magnetic band in the set in a textile sheath, and for each sheath to be fastenable around the affected body part by means of a fastener, preferably a hook-and-pile fastener.

The present invention provides an apparatus comprising at least two magnetic bands, each band capable of circumscribing an affected body part and being attached to the affected body part in an axially spaced-apart configuration. In a preferred embodiment, the apparatus comprises a set of three magnetic bands. In that case, a first magnetic band in the set is fastenable around the wrist of a wearer, and the second and third bands in the set are fastenable, respectively, around the arm of the wearer on opposite sides of the elbow joint. The second and third bands can be connected to each other by a connecting element. When used, the connecting element is preferably a strip of elastomeric fabric.

Yet another embodiment of the present invention provides a magnetic band having attached thereto at least one discrete rare earth magnet. The magnetic band is capable of being fastened to an affected body part.

In a preferred embodiment, a rare earth magnet on a first magnetic band can be positionable directly over the carpal tunnel of the wearer when the first band is fastened around the wrist of the wearer in use. Two rare earth magnets can preferably be provided on the second band, which can be fastened below the elbow joint of the wearer, such that the two rare earth magnets can be positioned on the inner forearm of the wearer when the second band is fastened around the arm of the wearer in use. A rare earth magnet can preferably be provided on the third band and can be positioned directly on the lower bicep of the wearer when the third band is fastened around the arm of the wearer in use.

Although this embodiment will be described with particular reference to the prevention and treatment of arm pump-up, the use of the invention is not limited to this application.

Figure 2:
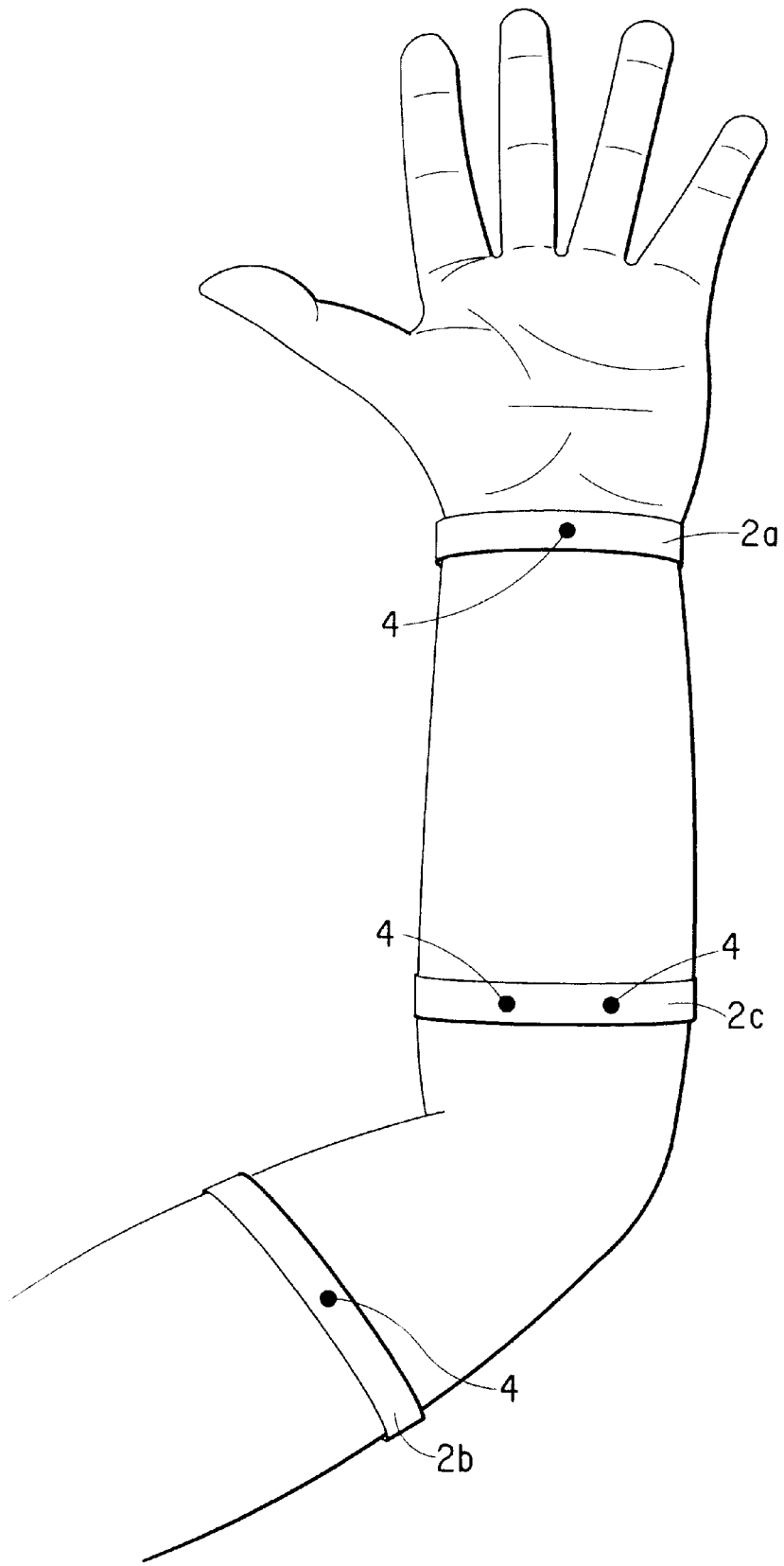
FIG. 2 is a perspective view of the apparatus of FIG. 1 shown in use on the arm of a wearer.

Referring to FIGS. 1 and 2, in which like features of the invention are indicated by like numerals, an apparatus for treating painful joint and muscle conditions is indicated generally by reference numeral 1.

As shown in the Figures, the apparatus 1 includes a set of three elongate magnetic bands 2a, 2b and 2c. Each magnetic band includes a flexible, rectangular member or strip 3a, 3b and 3c having major and minor axes. The major axis of each flexible, rectangular member is long enough to circumscribe a limb of a wearer thereof, such as an arm or a leg. The rectangular members 3a, 3b and 3c are made of a variety of materials that exhibit the desired combination of flexibility and magnetic force. Preferred materials include polymer bonded strontium and barium foil which is impregnated with a ferrite isotropic magnet. The isotropic magnet has a strength of about from 12000 to 16000 gauss with an energy product of between 0.3 and 0.4 mega-oersteds and a coercive force of about from 11000 to 12000 gauss.

Rare earth magnets 4 are attached to each flexible rectangular member 3a, 3b and 3c. The rare earth magnets 4 can be nickel-plated neodymium iron boron magnets which have a magnetic strength of about from 11000 to 12500 gauss with a coercive force of about from 10500 to 11000 gauss and an energy product of about from 20 to 30 mega-oersteds. The rare earth magnets 4 can be adhesively bonded to the flexible rectangular members 3a, 3b and 3c. The first two magnetic bands 2a and 2b include a single rare earth magnet 4 while the third band 2c incorporates two rare earth magnets 4 in a spaced-apart configuration.

Each magnetic band 2a, 2b and 2c in the set is enclosed in a respective textile sheath 5a, 5b and 5c. The textile sheath can be made of any fabric which is comfortable to the human touch. Each sheath 5a, 5b and 5c incorporates a preferred hook-and-pile fastener 6 to enable the magnetic band to be fastened around the arm of a wearer. The longer magnetic bands 2b and 2c in the set are connected to each other by a transverse strip of elastomeric fabric which is sewn to the respective textile sheaths 3b and 3c of the magnetic bands.

Figure 3:
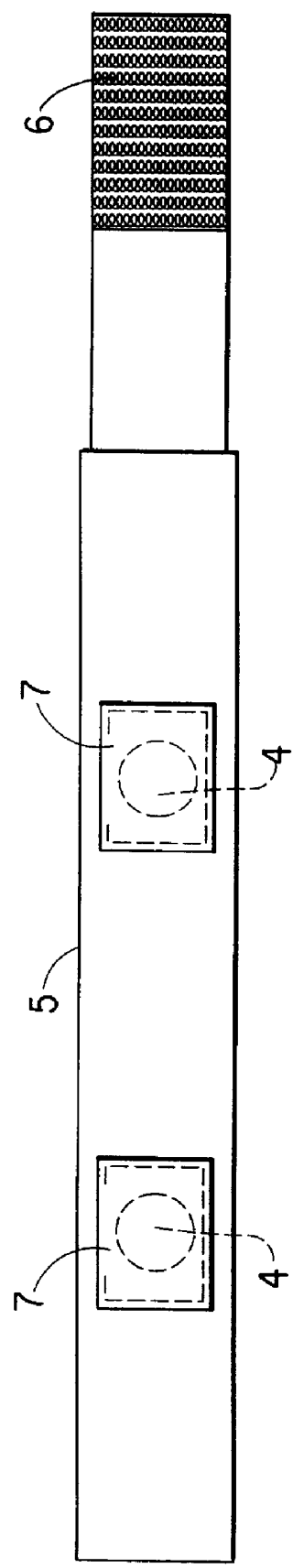
FIG. 3 is a preferred embodiment of the invention, incorporating pockets for the retention of discrete magnets.

In a preferred embodiment of the invention, as shown in FIG. 3, the rare earth magnets 4 can be attached to each flexible rectangular member by using pockets 7 sewn into the textile sheaths 5 which enclose the magnetic bands. Several pockets may be sewn into each textile sheath such that the positions of the rare earth magnets may be easily changed to modify the treatment of the affected body part.

In use, the set of magnetic bands 1 is fastened around an arm of a wearer as illustrated in FIG. 2. The shorter of the magnetic bands 2a is fastened around the wrist of the wearer so that the rare earth magnet 4 of this magnetic band is positioned directly over the carpal tunnel of the wearer. The transversely connected magnetic bands 2b and 2c are located respectively around the arm of the wearer on opposite sides of the elbow joint as indicated. The second and third magnetic bands are positioned such that, in use, the two rare earth magnets on the second magnetic band are positioned on the inner forearm of the wearer, while the single rare earth magnet on the third magnetic band 2b is positioned directly on the lower bicep of the wearer. A corresponding set of magnetic bands 2a, 2b and 2c may be fastened in an analogous manner to the other arm of the wearer.

It has been found that use of the magnetic bands as described above, by moto-cross or enduro riders, prevents the onset of the condition known as arm pump-up. Further, the set of magnetic bands 1 has been found to promote rapid recovery of persons already suffering from arm pump-up.

It will be appreciated by those skilled in the art that numerous modifications are possible to this embodiment without departing from the scope of the invention. In particular, the strength of the magnetic foil and the number of rare earth magnets on each magnetic band 2a, 2b and 2c can be altered or varied to suit the needs of a particular application.

The apparatus can also be conveniently applied to prevent or treat other conditions such as arthritis and muscle cramps. Further, the apparatus can be used on other body parts of a wearer such as a wearer's legs in order to treat knee problems.

I claim:

1. An apparatus for treating joint or muscle pain comprising a magnetic band having attached thereto at least one discrete rare earth magnet, the magnetic band adapted to be fastened to an affected body part, wherein the magnetic band comprises a flexible rectangular member having major and minor axes, the major axis being of a length such as to circumscribe the affected limb, the rectangular members comprising polymer-bonded strontium covered by a barium foil, and the barium foil being impregnated with a ferrite isotropic magnet.

2. An apparatus for treating joint or muscle pain, comprising at least two magnetic bands, each magnetic band adapted for circumscribing the affected limb and being attached to an affected body part in an axially spaced-apart configuration, wherein each magnetic band comprises a flexible rectangular member having major and minor axes, the major axis being of a length such as to circumscribe the affected limb, the rectangular members comprising polymer-bonded strontium covered by a barium foil, and the barium foil being impregnated with a ferrite isotropic magnet.

3. An apparatus of claim 1 wherein the ferrite isotropic magnets comprises a magnetic strength of about from 12000 to 16000 gauss.

4. An apparatus of claim 3 wherein the magnetic strength of the ferrite isotropic magnet is about 14000 gauss.

5. An apparatus of claim 1 wherein the ferrite isotropic magnets comprise an energy product of about from 0.3 to 0.4 mega-oersteds.

6. An apparatus of claim 5 wherein the ferrite isotropic magnets comprise an energy product of about 0.36 mega-oersteds.

7. An apparatus of claim 1 wherein the ferrite isotropic magnets comprise a coercive force of about from 11000 to 12000 gauss.

8. An apparatus of claim 7 wherein the ferrite isotropic magnets comprise a coercive force of about 11500 gauss.

9. An apparatus of claim 1 further comprising at least one rare earth magnet attached to each flexible rectangular member, the rare earth magnets comprise a magnetic strength of about from 11000 to 12500 gauss, a coercive force of about from 10500 to 11300 gauss, and an energy product of about from 30 to 40 mega-oersteds.

10. An apparatus of claim 9 wherein the rare earth magnets comprise nickel-plated neodymium iron boron comprise a magnetic strength of about from 11600 to 12300 gauss, a coercive force of about from 10800 to 11300 gauss, and an energy product of between about from 32 to 35 mega-oersteds.

11. An apparatus of claim 9 wherein the rare earth magnets are adhesively bonded to the flexible rectangular members.

12. An apparatus of claim 1 further comprising a textile sheath enclosing each magnetic band, each sheath having fastening means for securing the sheath around the affected body part.

13. An apparatus of claim 12 wherein the fastening means is a hook-and-pile fastener.

14. An apparatus of claim 12 further comprising means of connecting the second and third magnetic bands.

15. An apparatus of claim 14 wherein the means of connecting comprises a strip of elastomeric fabric.

16. An apparatus of claim 12 wherein a first magnetic band is adapted to be fastened around the wrist of the wearer, a second magnetic band is fastened below the elbow joint of the wearer, and a third magnetic band is fastened above the elbow joint of the wearer.

17. An apparatus of claim 16 wherein a first rare earth magnet is attached to the first magnetic band such that the first rare earth magnet are adapted to be positioned over the carpal tunnel region of the wrist, second and third rare earth magnets are attached to the second magnetic band such that the second and third rare earth magnets are adapted to be positioned over the inner forearm region, and a fourth rare earth magnet is attached to the third magnetic member such that the fourth rare earth magnet is adapted to be positioned over the lower bicep region.

18. An apparatus of claim 12 further comprising at least one pocket sewn into at least one of the textile sheaths, the at least one pocket adapted to receiving and containing at least one rare earth magnet, the at least one rare earth magnet comprise a magnetic strength of about from 11000 to 12500 gauss, a coercive force of about from 10500 to 11300 gauss, and an energy product of about from 30 to 40 mega-oersteds.

19. A method of treating joint or muscle pain, comprising circumscribing an affected body part by at least two magnetic bands in an axially spaced-apart configuration; wherein each magnetic band comprises a flexible rectangular member having major and minor axes, the major axis being of a length such as to circumscribe the affected limb, the rectangular members comprising polymer-bonded strontium covered by a barium foil, and the barium foil being impregnated with a ferrite isotropic magnet.

20. A method of claim 19 wherein the affected body part is an arm and wherein the method further comprises circumscribing the arm with at least three magnetic bands, wherein a first magnetic band is located around a wrist, and second and third magnetic bands are located on proximal and distal sides of an elbow joint.

21. A method of claim 20 further comprising the steps of:

a. placing a first discrete magnet on the first magnetic band over the carpal tunnel region;

b. placing second and third discrete magnets on the second magnetic band over the inner forearm; and c. placing a fourth discrete magnet on the third magnetic band over the lower bicep.

* * * * *